(12) United States Patent
Lyon

(10) Patent No.: US 6,733,573 B2
(45) Date of Patent: May 11, 2004

(54) CATALYST ALLOWING CONVERSION OF NATURAL GAS HYDRATE AND LIQUID $CO_2$ TO $CO_2$ HYDRATE AND NATURAL GAS

(75) Inventor: Richard Kenneth Lyon, Pittstown, NJ (US)

(73) Assignee: General Electric Company, Schenectady, NY (US)

(*) Notice: Subject to any disclaimer, the term of this patent is extended or adjusted under 35 U.S.C. 154(b) by 43 days.

(21) Appl. No.: 10/256,132

(22) Filed: Sep. 27, 2002

(65) Prior Publication Data

US 2004/0060438 A1 Apr. 1, 2004

(51) Int. Cl.[7] .................. C01B 31/20; E21B 43/16; C10L 3/06
(52) U.S. Cl. .................. 95/153; 95/237; 166/402; 423/220; 423/437.1; 585/15
(58) Field of Search .................. 95/236, 237, 153; 585/15; 166/266, 267, 402; 423/220, 226, 245.1, 437.1

(56) References Cited

U.S. PATENT DOCUMENTS

| | | | | |
|---|---|---|---|---|
| 4,007,787 A | * | 2/1977 | Cottle | 166/267 |
| 4,424,858 A | * | 1/1984 | Elliott et al. | 166/52 |
| 4,424,866 A | * | 1/1984 | McGuire | 166/303 |
| 5,261,490 A | * | 11/1993 | Ebinuma | 166/266 |
| 5,473,904 A | * | 12/1995 | Guo et al. | 62/46.1 |
| 5,536,893 A | * | 7/1996 | Gudmundsson | 585/15 |
| 5,562,891 A | * | 10/1996 | Spencer et al. | 423/437.1 |
| 5,713,416 A | * | 2/1998 | Chatterji et al. | 166/263 |
| 5,950,732 A | * | 9/1999 | Agee et al. | 166/354 |
| 6,028,234 A | * | 2/2000 | Heinemann et al. | 585/15 |
| 6,028,235 A | * | 2/2000 | Heinemann et al. | 585/15 |
| 6,389,820 B1 | * | 5/2002 | Rogers et al. | 62/45.1 |
| 6,602,326 B2 | * | 8/2003 | Lee et al. | 95/153 |
| 6,653,516 B1 | * | 11/2003 | Yoshikawa et al. | 585/15 |

OTHER PUBLICATIONS

Japan, Komai et al, Preprints Div. of Fuel Chemistry, ACS National Meeting 1997, San Francisco, 568–572.
"Clathrate Hydrates of Natural Gases" by E. Dendy Sloan, Jr., Marcel Dekker, Inc., New York 1998.
Herzog et al: "Environmental Impacts of Ocean Disposal of $CO_2$," Energy Convers. Mgmt, vol. 37, No. 608, pp. 99–1005, 1996.

* cited by examiner

Primary Examiner—Duane S. Smith
(74) Attorney, Agent, or Firm—Nixon & Vanderhye P.C.

(57) ABSTRACT

A method for recovering large volumes of hydrocarbon fuels, particularly methane ($CH_4$), using commercially available reagents which are strongly water-soluble and soluble in liquid $CO_2$ in the presence of liquid $CO_2$ injected into the methane hydrate formation. The reagents which are strongly water-soluble and soluble in liquid $CO_2$ form dilute aqueous acids that significantly increase the rate of conversion of methane hydrate into methane and $CO_2$ hydrate, thereby allowing the natural gas to be released in a form that can then be recovered in large quantities using conventional devices. The preferred embodiment uses $SO_3$, HCl or other strongly water soluble gas to cause the methane hydrate ice crystals to melt and form an aqueous solution. The aqueous solution contacts the methane hydrate ice on one side and liquid carbon dioxide on the other side. The system spontaneously adjusts so that the acid solution remains strong enough to melt the methane ice, but not strong enough to prevent the formation of the carbon dioxide ice at the recovery temperature and pressure. The natural gas is liberated from the hydrate and removed by conventional devices.

7 Claims, 5 Drawing Sheets

Relative Stabilities of CH4 and CO2 Hydrates

Permafrost = 610m
Temperature Pressure Gradient = 11.311kpa/m
Geothermal Gradient = 3.2C/100m

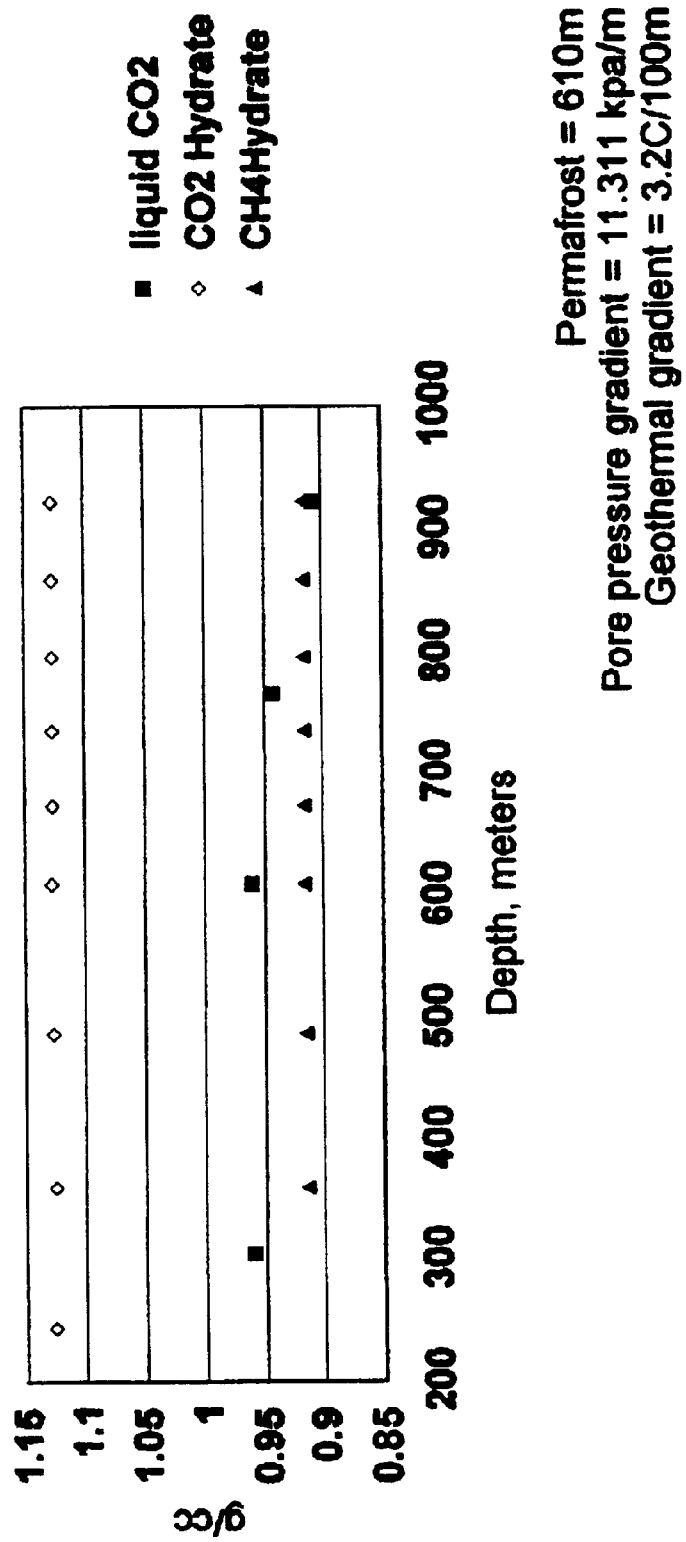

Condition of a Methane Hydrate Deposit prior to injection of liquid CO2

Condition of a Methane Hydrate Deposit after injection of liquid CO2 alone

Condition of a Methane Hydrate Deposit after injection of liquid CO2 and SO3

CATALYST ALLOWING CONVERSION OF NATURAL GAS HYDRATE AND LIQUID $CO_2$ TO $CO_2$ HYDRATE AND NATURAL GAS

BACKGROUND OF THE INVENTION

The present invention relates to the recovery of natural gas hydrate to produce large volumes of useable hydrocarbon fuels, particularly methane ($CH_4$). In particular, the present invention involves the use of an inexpensive and commercially available acid catalyst that allows natural gas hydrate and liquid $CO_2$ to be converted into $CO_2$ hydrate and natural gas in a form that can then be readily recovered using conventional means. The present invention has the added benefit of providing a cost-effective and environmentally safe method for disposing of $CO_2$ used during conversion of the hydrate.

Natural gas hydrate is a methane-bearing, ice-like material that occurs in abundance in marine and arctic sediments. The hydrate contains large amounts of methane in a "cage" of water ice molecules surrounding the gas, typically over 160 volumes of gas per unit volume of water (at nominal pressures and temperatures). Methane hydrates are known to form and remain stable at moderately high pressures and low temperatures, i.e., the conditions found on land in permafrost regions and within ocean floor sediments at water depths greater than about 500 meters. The increasing heat encountered in deeper sediments tends to preclude hydrate formation toward the bottom of the hydrate zone. Although free natural gas can be found in sediments below the hydrate zone, the hydrate deposits themselves, which may be several hundred meters thick, remain a vast and relatively untapped natural resource.

Methane hydrates have been detected around most continental margins, for example in Alaska, the west coast from California to Washington state, the east coast, including the Blake Ridge offshore the Carolinas, and in the Gulf of Mexico. Most scientists believe that at least 200,000 tcf of methane exists in hydrate systems located in the U.S. permafrost regions and surrounding waters. That amount is hundreds of times larger than the total estimated U.S. natural gas reserves. Most estimates of U.S. hydrate resources range between 112,000 tcf and 676,000 tcf (at 0.95 and 0.05 probability levels respectively, with the mean value being approximately 200,000 tcf). The amount of offshore hydrate is estimated to be about 99% of that total. Thus, if only 1% of the estimated 200,000 tcf methane hydrate resource became economically recoverable, the domestic U.S. natural gas resource could at least double.

It is well known that the U.S. will consume increasing volumes of natural gas in the $21^{st}$ century. Thus, methane hydrates could become a reliable, low cost domestic supply, particularly when used for power generation, transportation or even fuel cells due to the increasing pressure for cleaner fuels with reduced $CO_2$, particulates, sulfur oxides, and nitrogen oxides.

Although the estimated reserves of natural gas hydrate are larger than the reserves of all other fossil fuels combined, the technology necessary to recover large amounts of natural gas from hydrate has never proven to be economically feasible. Thus, with one exception in Russia (discussed below), natural gas hydrate has not been used to generate recoverable fuel in commercially significant amounts.

A Department of Energy report ("Draft Methane Hydrate program Plan, April 1998"), available on the internet at www.fe.doe.gov discusses various proposed methods of producing natural gas from hydrate deposits. One method proposes that hot water be pumped down into the deposit to melt the solid hydrate into liquid water and gaseous methane. The heat necessary to do this, however, approaches that necessary to melt an equivalent amount of ice. Since hydrate deposits are relatively "thin" geological structures spread out over large areas, supplying such a large amount of heat in the form of hot water would be very expensive and logistically difficult. Furthermore, converting the massive amounts of solid hydrate into liquid water may have undesirable environmental effects. For example, a concern exists that converting solid hydrate to water may cause geological instability at or near the deposit. The possibility also exists that large amounts of methane liberated during the conversion process might escape into the atmosphere. In addition to posing an immediate health risk to persons living or working in the area, such uncontrolled emissions could add to the greenhouse effect.

The DOE report also discusses using indirect heating techniques to convert hydrate deposits into natural gas and liquid water. Unfortunately, changing the way the heat is supplied does not change the amount of heat that must be supplied. Thus, the same environmental concerns exist with the conversion of large volumes of solid hydrate into liquid to liberate methane gas, regardless of the heat source.

Recently, scientists have recognized that carbon dioxide hydrate, i.e., $CO_2$ encased within water-ice molecules, is more stable than natural gas hydrate at the same depth, i.e., at a given pressure and temperature. Thus, geologists have now postulated that it may be possible to use carbon dioxide hydrate to liberate the methane in the natural gas hydrate. However, even though carbon dioxide hydrate is known to be more stable than methane hydrate with certain pressure and temperature ranges, one will not readily convert to the other. Because natural gas hydrate does not readily absorb the carbon dioxide (and vice versa) only the hydrate close to the surface of the ice will reject one absorbed material to accept another. Thus, the inside of the hydrate remains essentially unchanged.

One known prior art technique for recovering methane developed in Japan, Komai et al, "Preprints Div. of Fuel Chemistry, ACS national Meeting 1997, San Francisco, 568–572) has suggested injecting liquid $CO_2$ directly into the hydrate zone to convert methane hydrate into methane and $CO_2$ hydrate. Since the reaction is very nearly thermoneutral, this technique eliminates the need to supply heat to the hydrate. The Komai et al method also avoids some of the environmental concerns relating to the conversion of one solid hydrate into a liquid because a solid hydrate is converted into another solid hydrate of different composition and form.

The Komai et al methodology suffers from a number of critical limitations primarily because methane hydrate is thermodynamically stable under only a limited range of temperatures and pressure. As noted above, hydrate deposits tend to exist as geologically "thin" layers compared to other fossil fuel resources. The deposits also tend to be spread out over large geographic areas, making conventional recovery techniques less economically viable. The hydrate also tends to form under impermeable geological formations ("caps"). As the process of converting liquid water (and ice) to solid hydrate goes to completion over many thousands of years, the conversion process leaves behind a dry, nonporous mixture of sand and hydrate known as overburden.

When liquid $CO_2$ (or some other liquid) is pumped into the ground at a pressure that exceeds the weight of the overburden (as suggested in Komai et al), after an extended time period the substratum may fracture, with the cracks spreading horizontally. Thus, even though it may be technically feasible to inject liquid $CO_2$ into a hydrate formation to allow the $CO_2$ to contact a large area of the hydrate deposit, the Komai et al process is not economically practical on a large scale unless the reaction of liquid $CO_2$ and methane hydrate to form $CO_2$ hydrate and gaseous methane could be made to occur at a much higher rate. Generally speaking, if the hydrate of gas A is in direct contact with molecules of gas B, then the molecules of gas A on the surface of the hydrate will diffuse out to be replaced by the molecules of gas B which diffuse into the surface openings. If gas B is the more stable hydrate, the surface of the first hydrate particle will readily be converted from A to B, with the rate of conversion of the bulk hydrate from A to B being controlled by diffusion through the solid phase (normally a very slow process). When the reaction of liquid $CO_2$ with the methane hydrate to form $CO_2$ hydrate and gaseous methane is slow, the rate of production of natural gas will likely be too slow to be economically viable. In addition, the amount of liquid $CO_2$ that accumulates underground over an extended time period of time during the conversion could become large and create additional environmental and geological concerns. Unfortunately, the Komai et al reference provides no teaching as to how an acceptably high rate of hydrate conversion may be achieved.

BRIEF DESCRIPTION OF THE INVENTION

The present invention solves the problem of $CO_2$ disposal while producing natural gas from hydrate by providing a new and more efficient method for converting liquid $CO_2$ and natural gas hydrate into natural gas and $CO_2$ hydrate, and thereafter recovering the natural gas product using conventional means. In particular, the invention provides a means whereby the conversion of $CO_2$ and methane hydrate to $CO_2$ hydrate and gaseous methane occurs much more rapidly than Komai et al, thereby reducing the cost of producing natural gas while avoiding any serious environmental concerns.

The invention takes advantage of the relative differences in density between liquid $CO_2$, methane hydrate and $CO_2$ hydrate at a given field depth. That is, the method according to the invention uses the predicted differential in density to facilitate the conversion of methane hydrate to $CO_2$ hydrate, with the added beneficial result being the release of methane gas from the hydrate.

It has now been discovered that the use of $SO_3$ or HCl or other reagents which are strongly water-soluble and soluble in liquid $CO_2$ in combination with liquid $CO_2$ injected into the hydrate zone will cause the methane hydrate ice crystals to melt and form a layer of water. On one side, this aqueous phase contacts the methane hydrate ice and, on the other side, contacts the, liquid carbon dioxide. The melting of the ice dilutes the HCl or the sulfuric acid, which in turn tends to become lower in concentration until it no longer melts the methane hydrate. Conversely the removal of water from the solution by the formation of $CO_2$ hydrate tends to increase the concentration and restore its ability to melt the methane hydrate. The system spontaneously adjusts so that the aqueous acid solution remains strong enough to melt methane ice, but not strong enough to prevent the formation of the carbon dioxide ice, which is more thermodynamically stable at the same depth. Thus, on one side of the aqueous solution the methane ice melts, and on the other side carbon dioxide ice forms. This catalyst "trick" results in dramatically better methane formation and recovery rates, primarily because the liberation of methane is no longer limited to amount of methane which was initially at or near the surface of the hydrate. Instead the continual melting of the methane hydrate and freezing of carbon dioxide hydrate provide a facile mechanism for freeing the methane.

BRIEF DESCRIPTION OF THE DRAWINGS

FIG. 2 shows the density of liquid carbon dioxide, $CO_2$ hydrate and $CH_4$ hydrate in grams per cc plotted as a function of depth below the earth's surface in meters;

DETAILED DESCRIPTION OF THE INVENTION

Figure 1:
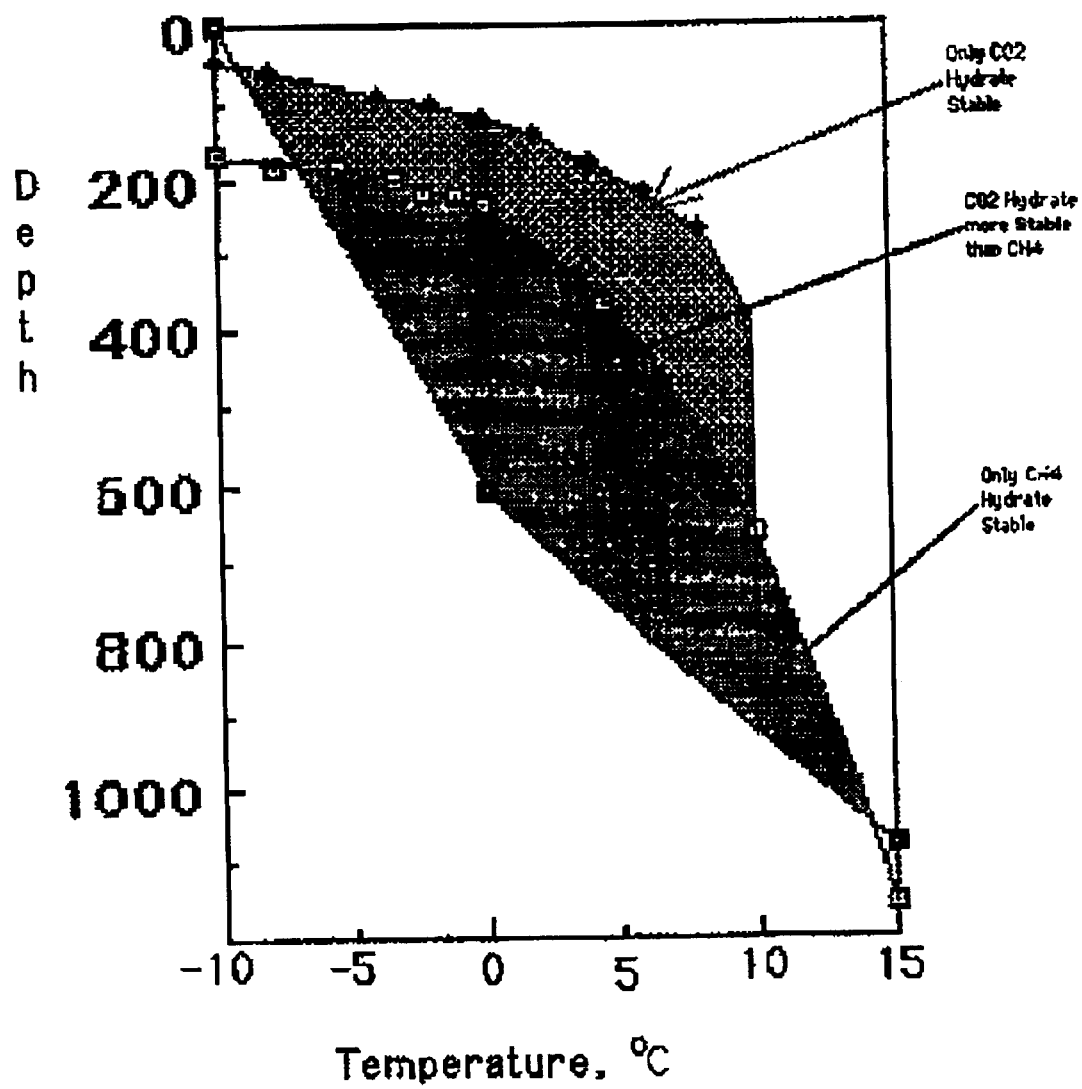
FIG. 1 is a graphical representation of the relative stabilities of methane and carbon dioxide hydrates at various geological depths plotted against temperature.

As noted above, it has now been found that the use of certain catalyst materials, preferably sulfur trioxide or HCl, can cause the methane hydrate to melt (thereby liberating the natural gas), while forming carbon dioxide hydrate as a product of the reaction. FIG. 1 shows the results of thermodynamic calculations of the stability of methane and $CO_2$ hydrate as a function of depth using the computer program described in "Clathrate Hydrates of Natural Gases" by E. Dendy Sloan, Jr., Marcel Dekker, Inc., New York 1998. The calculations were done for a typical hydrate deposit. The deposit was assumed to be in a region with an average temperature of $-10°$ C., with a permafrost depth of 610 m, a geothermal temperature gradient of $3.2°$ C./100 meters and a pore pressure gradient of 11.311 kpa per meter. In practical terms, the deposit would be located in the far north (or the far south) where the average temperature is about $-10°$ C. and the ground is frozen to a depth of 610 meters. Under the permafrost, the temperature increases at a nominal rate of $3.2°$ C. for every 100 meters increase in depth; any underground liquids or gases are under a pressure that increases by about 11.311 kpa per meter.

As FIG. 1 illustrates, hydrate tends to form in three geological zones—one with only $CO_2$ hydrate, one in which only methane hydrate can exist, and one in which both hydrates exist but with the $CO_2$ hydrate being more thermodynamically stable. This last zone is particularly useful in practicing the recovery method according to the invention.

FIG. 2 shows the calculated density of methane hydrate, $CO_2$ hydrate, and liquid $CO_2$ as a function of depth in a typical hydrate formations. Although a wide range of temperature/pressure conditions exist under which $CO_2$ hydrate is more stable than methane hydrate, direct contact between the liquid $CO_2$ and the solid hydrate will only convert the surface of the hydrate, i.e., a trivially small fraction of the total hydrate. The use of $SO_3$ or HCl catalysts as discussed above changes the entire dynamic of the conversion process by allowing methane far below the original hydrate surface to eventually be liberated as the conversion process from methane hydrate to $CO_2$ hydrate progresses. That is, as the ice melts, it continuously forms a new aqueous layer containing the acid catalyst and continues to liberate more methane within the lower recesses of the hydrate as the melting proceeds and $CO_2$ hydrate continues to form. The exact amount of $SO_3$ and HCl necessary to create the aqueous layer is not critical, provided the amount is not so high that it impedes the formation of the $CO_2$ hydrate layer.

Another aspect of the subject invention relies on the known fact that $CO_2$ recovered from fossil fuel combustion typically contains at least a few hundred ppm $SO_2$. The $SO_2$ can easily be converted into $SO_3$ by various processes known in the art, e.g., by reaction with $H_2O_2$. Thus, an alternative embodiment of the present invention eliminates the step of adding $SO_3$ and instead injects $H_2O_2$ which then reacts with the $SO_2$ already present in the liquid $CO_2$.

Under either process described above, when the liquid $CO_2$ contacts the methane hydrate, it converts the surface of the hydrate to $CO_2$ hydrate. Again, as the $SO_3$ diffuses into the methane hydrate ice surface, it reacts to form dilute sulfuric acid. Since sulfuric acid is strongly hygroscopic, it tends to pull water out of the hydrate. This removes the surface layer of $CO_2$ hydrate and leaves the surface coated with a thin layer of dilute sulfuric acid. Additional methane hydrate can then be dissolved and additional $CO_2$ hydrate precipitates. The process continues until much of the methane hydrate in the formation has been converted. The methane gas is then removed by conventional means.

As shown in FIG. 2 above, liquid $CO_2$ is less dense than $CO_2$ hydrate but more dense than methane hydrate. Thus, as the conversion of the hydrate deposit proceeds, the liquid $CO_2$ will tend to remain under the methane hydrate while floating on the $CO_2$ hydrate. As a result, relatively good conversion of the hydrate deposit may be achieved at a much higher rate, particularly as compared to the prior art Komai et al method. FIG. 3 shows the reaction sequence that occurs when generating free methane in accordance with the invention. The recovery of natural gas from the hydrate occurs as the methane is continuously liberated during the conversion reaction forming $CO_2$ hydrate.

Figure 3A:
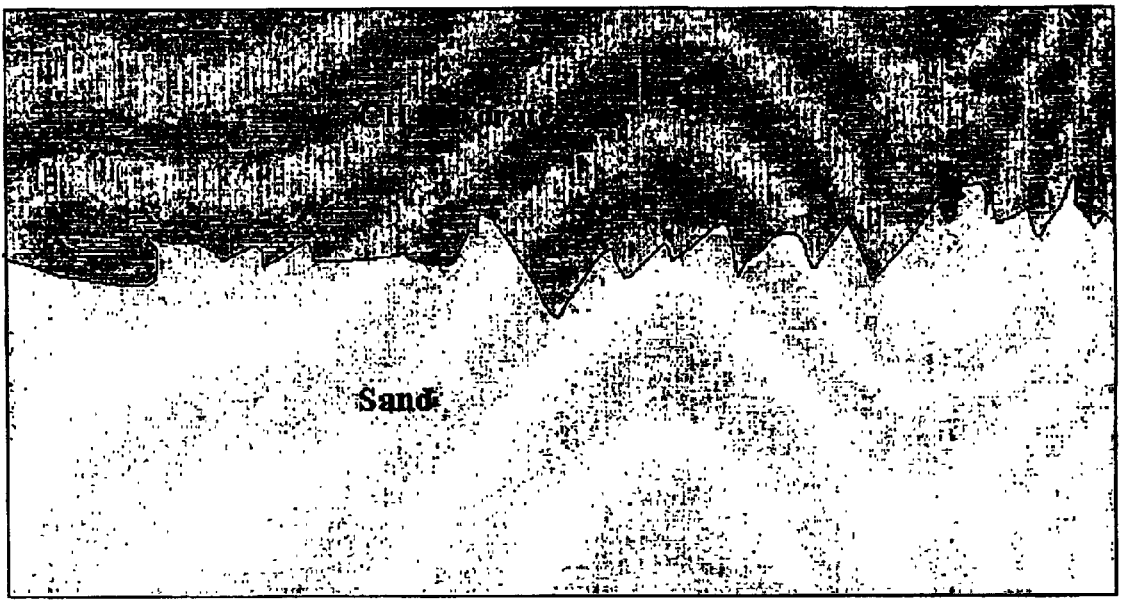
FIG. 3a illustrates the condition of a methane hydrate deposit prior to injection of liquid $CO_2$.
Figure 3B:
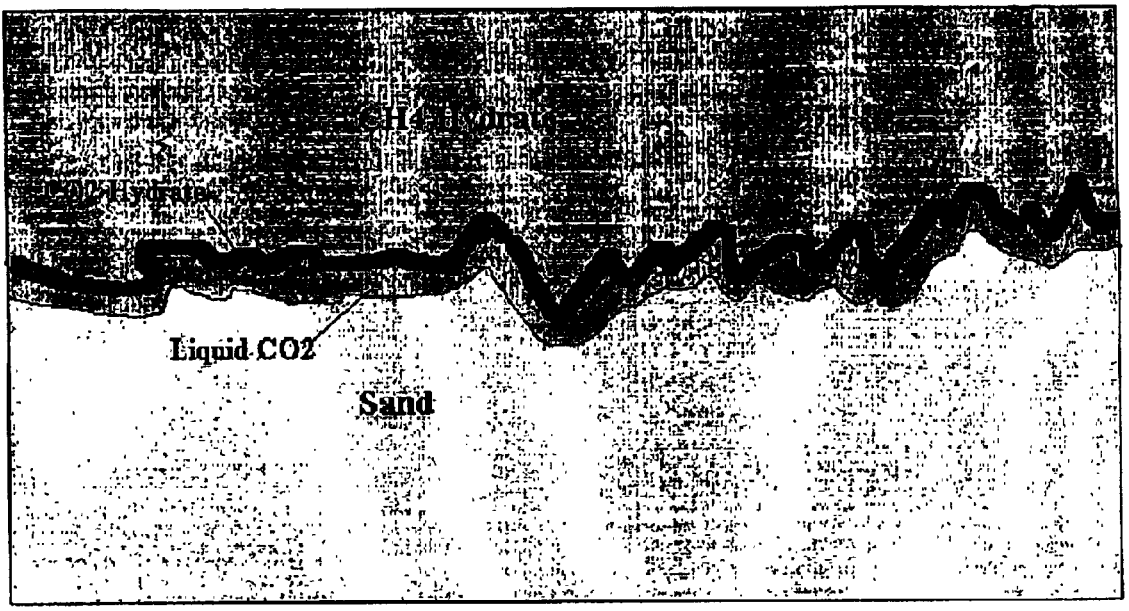
FIG. 3b shows the condition of a methane hydrate deposit after injection of liquid $CO_2$ alone.
Figure 3:
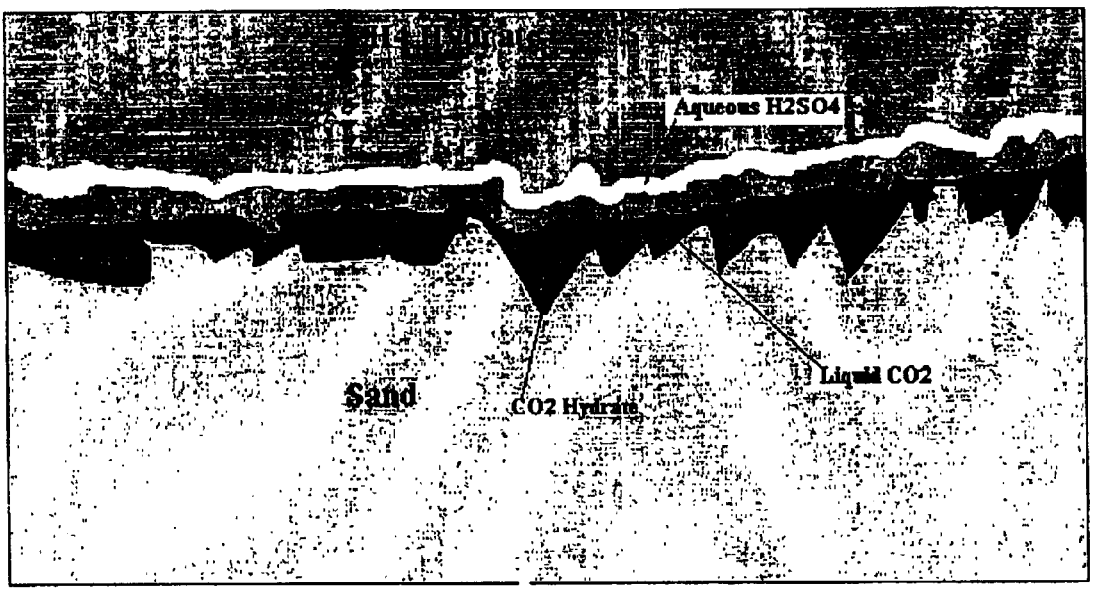
FIG. 3c depicts the condition of a methane hydrate deposit after injection of liquid $CO_2$ and $SO_3$.

FIGS. 3a, 3b, and 3c depict the general reaction sequence that occurs when liquid carbon dioxide alone is injected into the methane hydrate (FIG. 3b) and in the presence of $SO_3$ or HCl or some other substance which readily forms an aqueous solution (FIG. 3c). FIG. 3a depicts the methane hydrate prior to the injection of liquid $CO_2$. The methane hydrate is depicted as a layer resting on the sand. FIG. 3b depicts the situation which occurs when liquid $CO_2$ alone is injected. The liquid $CO_2$ is depicted as a layer between the methane hydrate and the sand. The $CO_2$ hydrate (depicted in a darker gray shade in FIG. 3b) forms only as a thin layer between the methane hydrate and the liquid $CO_2$. FIG. 3c depicts the situation which occurs when liquid $CO_2$ is injected along with $SO_3$. A layer of aqueous $H_2SO_4$ forms between the methane hydrate and the liquid $CO_2$. This layer is shown in white in FIG. 3c. At the interface between the aqueous $H_2SO_4$ and the $CH_4$ hydrate, water and natural gas are liberated with the natural gas escaping. At the interface between the aqueous $H_2SO_4$ and the liquid $CO_2$ water and $CO_2$ are converted into $CO_2$ hydrate. The $CO_2$ hydrate is, however, more dense than liquid $CO_2$ and hence instead of accumulating at the interface falls to the bottom of the liquid $CO_2$ layer and accumulates there.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method for recovering methane gas from a methane hydrate formation comprising the steps of:

injecting liquid $CO_2$ and a reagent which are strongly water-soluble and soluble in liquid $CO_2$ into the methane hydrate formation in an amount sufficient to convert a substantial portion of the methane hydrate into $CO_2$ hydrate and methane gas;

whereby said strongly water soluble reagent dissolves some of the methane hydrate, thereby forming a layer of dilute aqueous solution between said methane hydrate formation and said layer of liquid $CO_2$ and causing the release of methane gas contained in said surface layer of methane hydrate; and whereby a layer of $CO_2$ hydrate forms as said surface layer of methane hydrate is dissolved; and collecting and removing said methane gas after it is released from said methane hydrate.

2. A method according to claim 1, wherein said water soluble reagent comprises $SO_3$.

3. A method according to claim 1, wherein said water soluble reagent comprises HCl.

4. A method according to claim 1, wherein said step of injecting said liquid $CO_2$ into said methane hydrate formation occurs at a pressure and temperature sufficient to ensure that the $CO_2$ hydrate remains more thermally stable than said methane hydrate during said conversion.

5. A method according to claim 1, wherein said step of injecting said liquid $CO_2$ results in the formation of a layer of liquid $CO_2$ below the methane hydrate.

6. A method according to claim 1, wherein said steps of injecting said liquid $CO_2$ and said water soluble reagent results in the formation of a layer of $CO_2$ hydrate below said liquid $CO_2$.

7. A method for recovering methane gas from a methane hydrate formation comprising the steps of:

injecting liquid $CO_2$ containing small amounts of $SO_2$ into said methane hydrate formation in an amount sufficient to allow the liquid $CO_2$ to form a layer below the methane hydrate at a pressure and temperature sufficient to convert a substantial portion of the methane hydrate into $CO_2$ hydrate and methane gas;

injecting $H_2O_2$ into said liquid $CO_2$ in an amount sufficient to convert the $SO_2$ into $SO_3$ gas; whereby said $SO_3$ gas dissolves a surface layer of methane hydrate, thereby forming a layer of dilute aqueous sulfuric acid between said methane hydrate formation and said layer of liquid $CO_2$ and causing the release of methane gas contained in said surface layer of methane hydrate;

and whereby a layer of $CO_2$ hydrate forms as said surface layer of methane hydrate is dissolved; and collecting and removing said methane gas after it is released from said methane hydrate.

* * * * *

UNITED STATES PATENT AND TRADEMARK OFFICE
CERTIFICATE OF CORRECTION

PATENT NO. : 6,733,573 B2
DATED : May 11, 2004
INVENTOR(S) : Lyon

It is certified that error appears in the above-identified patent and that said Letters Patent is hereby corrected as shown below:

<u>Column 1,</u>
Line 67, delete "www.fe.doe.gov" and insert -- http://www./fe./doe.gov/oil_gas/methanehydrates/hydrateplan.html --.

Signed and Sealed this

Thirtieth Day of November, 2004

JON W. DUDAS
*Director of the United States Patent and Trademark Office*